(12) United States Patent (10) Patent No.: US 8,961,482 B2
Heyman (45) Date of Patent: Feb. 24, 2015

(54) HYGIENIC ARTICLE

(76) Inventor: Ian A. Heyman, Pataskala, OH (US)

( * ) Notice: Subject to any disclaimer, the term of this patent is extended or adjusted under 35 U.S.C. 154(b) by 225 days.

(21) Appl. No.: 13/558,818

(22) Filed: Jul. 26, 2012

(65) Prior Publication Data

US 2013/0030401 A1 Jan. 31, 2013

Related U.S. Application Data

(60) Provisional application No. 61/512,709, filed on Jul. 28, 2011.

(51) Int. Cl.
*A61F 5/44* (2006.01)
*A61F 13/471* (2006.01)
*A61F 5/451* (2006.01)
*A61F 5/453* (2006.01)

(52) U.S. Cl.
CPC ............... *A61F 13/471* (2013.01); *A61F 5/451* (2013.01); *A61F 5/453* (2013.01)
USPC ............................ 604/349; 604/352; 604/354

(58) Field of Classification Search
CPC ......... A61F 5/44; A61F 5/4401; A61F 5/451; A61F 5/453; A61F 13/471; A61F 13/4915
USPC ...................... 604/349–354, 385.09
See application file for complete search history.

(56) References Cited

U.S. PATENT DOCUMENTS

| | | | |
|---|---|---|---|
| 2,873,740 A * | 2/1959 | Wainwright | 604/347 |
| 3,858,584 A * | 1/1975 | Johnson | 604/351 |
| 4,601,716 A * | 7/1986 | Smith | 604/349 |
| 4,790,835 A * | 12/1988 | Elias | 604/349 |
| 4,963,137 A | 10/1990 | Heyden | |
| 5,314,447 A | 5/1994 | Papurt | |
| 5,622,186 A | 4/1997 | Schwartz | |
| 5,643,235 A * | 7/1997 | Figuerido | 604/352 |
| 5,695,485 A * | 12/1997 | Duperret et al. | 604/349 |
| 5,855,206 A | 1/1999 | Ireland | |
| 6,059,762 A * | 5/2000 | Boyer et al. | 604/349 |
| 6,061,840 A | 5/2000 | Alligator | |
| 6,113,582 A * | 9/2000 | Dwork | 604/349 |
| 6,250,303 B1 | 6/2001 | Delaney | |
| 6,419,665 B1 | 7/2002 | Cohen | |
| 6,487,728 B1 | 12/2002 | Cook | |
| 6,580,011 B1 | 6/2003 | Jennings-Spring | |
| 6,846,508 B1 | 1/2005 | Colas et al. | |
| 7,137,972 B1 | 11/2006 | Holberg | |
| 7,527,589 B2 | 5/2009 | Squicciarini | |
| 7,669,253 B2 | 3/2010 | Lin | |
| 7,673,632 B1 | 3/2010 | Mistler | |
| 2003/0023222 A1 * | 1/2003 | Chen | 604/385.09 |
| 2007/0142794 A1 | 6/2007 | Bester, Jr. et al. | |
| 2013/0053804 A1 * | 2/2013 | Sorensen et al. | 604/349 |

* cited by examiner

*Primary Examiner* — Lynne Anderson

(74) *Attorney, Agent, or Firm* — Hahn Loeser + Parks LLP

(57) ABSTRACT

A hygienic article for a male is disclosed. The hygienic article includes a tube having a first end adapted to receive a limp penis and a closed second end, the elasticized tube being formed of breathable material, a retaining portion adjacent the first end of the tube adapted to retain the hygienic article on the penis without substantially constricting blood flow, and an absorbent material extending at least within the second end of the tube adapted to absorb fluids.

27 Claims, 3 Drawing Sheets

HYGIENIC ARTICLE

CROSS-REFERENCE TO RELATED APPLICATION

This application claims priority to U.S. Provisional Patent Application No. 61/512,709, filed Jul. 28, 2011, and entitled LEAKAGE PREVENTION APPARATUS, which is incorporated herein by reference.

BACKGROUND AND SUMMARY

This present disclosure is related to a hygienic article for males.

Incontinence in a man can arise for many reasons and at any age. For example vehicular accidents, sporting accidents, and any number of medical conditions can give rise to incontinence. Incontinence can also be a product of age, whereby a man's prostate becomes enlarged, surgery effects the nerves serving the bladder, or the man develops Alzheimer's disease or dementia. Incontinence in a man may present by the sporadic or continual trickling of urine from the penis, or may result in spontaneous release of the entire contents of the bladder.

In a hospital or nursing home catheters may be employed to direct the urine into a catchment bag for later disposal. Alternatively the catheter may be used to prevent the continuous or spontaneous release of urine until the patient or resident goes to the bathroom. Catheters are invasive to use and have been responsible for introducing infection, creating undesired health risks for an incontinent man.

Current substitutes to catheters designed to aid an incontinent man suffer from being conspicuous and bulky and may make noise when moving about. Thus they are embarrassing for males of any age to wear, and hamper mobility. Such incontinence products further suffer from not being tailored to target the specific area in which urine exits the body. Throughout the day a man's penis may not remain positioned such that urine may be collected into an incontinence pad or a diaper. This can cause embarrassment and is unhygienic. Furthermore the adult diaper or pad can be easily replaced only when a person is standing. The care giver will either have to move the patient or resident into a standing position, a task made especially challenging when a patient is also infirm and immobile, or continually roll and move the patient who is lying in bed to position the incontinence product underneath him. Among other problems, these obstacles may result in the incontinence diaper or pad being incorrectly positioned on the patient, or it may result in the incontinence diaper or pad being changed less frequently than desired. Additionally, the size of the conventional incontinence pad or diaper means that it will be in contact with areas of skin other than the person's penis. This provides for bodily fluids, such as urine, to be in contact, intermittently or continually, with a much greater area of the man's body, which is unsanitary and can cause skin irritation. Additionally, some prior male incontinence products have employed a clamping mechanism formed of plastic bars that pinch the penis to secure the product to the user. Such products have caused discomfort for user and also restrict blood flow in the penis often requiring that the product be periodically removed.

Using conventional incontinence products may have adverse psychological and emotional effects on the male wearer. For example the adult nappy or diaper may make the incontinent patient feel that he is being treated like a young child. Also, many incontinence products, such as the incontinence guard worn similarly to a woman's sanitary napkin, are associated with and have the appearance of products that a female might wear, causing the incontinent man to feel emasculated. The emotional and psychological effects associated with incontinence are compounded by the products currently available on the market. A male suffering from being incontinent is compelled to accept these emotional and psychological problems or is dissuaded from using the products altogether.

Male underwear garments are well known, such as, briefs, boxer shorts, boxer briefs, bikini briefs, thongs, jock straps, and variants thereof. Virtually every variant of male underwear includes a pouch for holding both the penis and scrotum. This construction may overly constrict or crowd the penis and scrotum, causing a reduction in blood flow to the genitals and potentially impairing, temporally or permanently, the function of the testicles. The over-crowding may also cause entanglements, sweating, sticking, irritation, abrasions, and misalignments.

The man who desires to be less confined by the constraints of the currently available underwear must forgo all protection and hygiene. This allows exposure to bodily fluids such as sweat and urine, which can cause damage to the skin due to excess moisture on the skin and also from irritation caused by the chemical makeup of the bodily fluids. Further harm to skin can arise from the friction between the man's penis and the inside surface of any clothing article the man may be wearing or the man's own thighs and groin area, and may exacerbate the irritant effects of sustained exposure to bodily fluids.

In view of the limitations of presently available products, there is a need for a hygienic article which can be easily and conveniently replaceable, and which offers the protection required by the incontinent male without the adverse emotional and psychological effects associated with products currently available. There is also a need for an article for a male to wear to overcome the problems with conventional underwear while offering hygienic protection.

Presently disclosed is a hygienic article for a male comprising a tube having a first end adapted to receive a limp penis and a closed second end, the tube being formed of breathable material, a retaining portion adjacent the first end of the tube adapted to retain the hygienic article on the penis without substantially constricting blood flow in the penis, and an absorbent material extending at least within the second end of the tube adapted to absorb fluids. The absorbent material may be provided with the tube or may be separately provided. In one embodiment, the absorbent material is may be replaced while the remainder of the hygienic article is reused.

The retaining portion may be adapted in many ways to retain the hygienic article on the penis. For example the retaining portion may comprise an elasticized band, or it may have elasticized thread woven into the breathable material of the tube adjacent the first end, both adapted to extend around the penis and to retain the hygienic article on the penis. Alternatively the retaining portion may comprise at least one elastic tie adapted to extend around the penis and to retain the hygienic article on the penis. Further the retaining portion may comprise at least one adhesive strip adapted to be secured to the penis or pelvic area to retain the hygienic article on the penis. The retaining portion may comprise silicone beading configured to retain the hygienic article on the penis.

DETAILED DESCRIPTION OF THE DRAWINGS

Presently disclosed is an easily replaced hygienic article for a male providing comfort and protection. The hygienic article may also protect against the effects of incontinence or unintended urination. The hygienic article may be easily applied regardless of the position or mobility of the man or the man's penis. The hygienic article for a male also allows the male wearer to be free of the confines of conventional underwear while still being afforded hygienic protection. Furthermore, the hygienic article for a male may be configured such as to be easily disposable.

Referring generally to FIGS. 1 through 7, a hygienic article for a male is disclosed. In one embodiment, the hygienic article comprises a tube having a first end adapted to receive a limp penis and a closed second end, where the tube is formed of breathable material. The hygienic article also includes a retaining portion adjacent the first end of the tube adapted to retain the hygienic article on the penis without substantially constricting blood flow in the penis, and an absorbent material extending at least within the second end of the tube adapted to absorb fluids. The absorbent material may be part of the tube or may be separately provided. In some embodiments, the absorbent material may be replaceable within the hygienic article.

Figure 1:
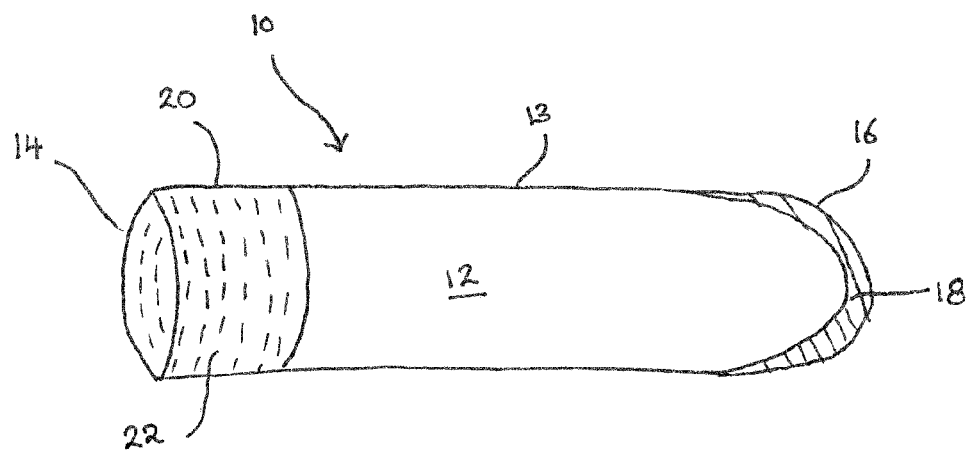
FIG. 1 is a perspective view of a first embodiment of a hygienic article for a male.

Referring to FIG. 1, one embodiment of a hygienic article 10 is illustrated. The hygienic article 10 has a tube 11. The tube 11 has a first end 14 adapted to receive a limp penis and a closed second end 16. The tube 11 is formed of breathable material 13. The hygienic article 10 also has a retaining portion 20 adjacent the first end 14 of the tube 11 adapted to retain the hygienic article 10 on the penis without substantially constricting blood flow in the penis, and an absorbent material 18 extending at least within the second end of the tube 11 adapted to absorb fluid. The first end 14 adapted to receive a limp penis may accommodate multiple size penises. In addition, it is contemplated that the hygienic article 10 will be produced in multiple sizes, in order to fit the individual needs of the wearer. In one embodiment, a portion of the tube 11 may be formed of elastic material to assist in retention of the hygienic article 10. The portion of the tube 11 formed of elastic material may be adjacent the first end of the tube 11. In another embodiment, the entire tube 11 may be formed from elastic material to form an elasticized tube.

In use, the absorbent material 18 may absorb fluids, such as urine. In various embodiments, the absorbent material 18 is adapted to absorb a desired amounts of fluid, such as, for example, only small amounts of urine or, in an alternative embodiment, an entire bladder-full of urine. The absorbent material 18 may be confined to a specific portion of the hygienic article 10, such as within the second end 16. Alternatively, the absorbent material 18 may extend substantially between the second end 16 and the first end 14, or the absorbent material 18 may extend throughout the entire length of the tube 11. Moreover, the absorbent material 18 may extend only partially around the circumference of the tube 11, or, as shown in FIG. 1, extend substantially around the circumference of the tube 11. In a further embodiment, described in detail below, the absorbent material 18 may be integral with the tube 11, and also integral with the breathable material 13. The absorbent material 18 may be made from natural materials, synthetic materials, or combinations of natural and synthetic materials, such as, cotton, hemp, sponge, wool, cork, synthetic sponge, polyester or polyester mixes, neoprene, plastics, synthetic cork, or fleece materials. The breathable material 13 may also be made of natural materials, synthetic materials, or combinations of natural and synthetic materials, such as, rayon, nylon, spandex, cotton, hemp, leather, Lycra, elastics, microfiber or wool, in addition to the materials previously mentioned. In one embodiment, the breathable material 13 comprises tubular stretch net material made from high quality nylon and rubber mix, and the absorbent material 18 comprises a sanitary towel or similar product material.

In the embodiment illustrated in FIG. 1, the retaining portion 20 is a band of elasticized thread 22 interwoven into the tube 11, extending substantially around the circumference of the hygienic article 10. The retaining portion 20 extends around the penis and retains the hygienic article 10 on the penis without substantially constricting blood flow in the penis. Alternatively, elasticized thread 22 may be intermittently interwoven into the tube 11, around the circumference of the hygienic article 10. In one embodiment, the retaining portion 20 is positioned at the first end 14 of the tube 11. In other embodiments, the retaining portion 20 may extend from the first end 14 of the tube. In yet other embodiments, the retaining portion 20 may be integrated with the tube 11 and may extend at least partially towards the second end 16 to achieve a desired retention force on the penis.

An incontinent male is able to wear the hygienic article 10 without the adverse emotional and psychological effects that are associated with adult nappies, diapers and incontinence pads. Furthermore, the hygienic article 10 may be more effectively retained on the penis in the proper position to received urine. The hygienic article 10 thus aids in preventing urine from coming into contact, temporarily or permanently, with other areas of the body, such as the upper thighs, buttocks, abdomen or scrotum.

Figure 2:
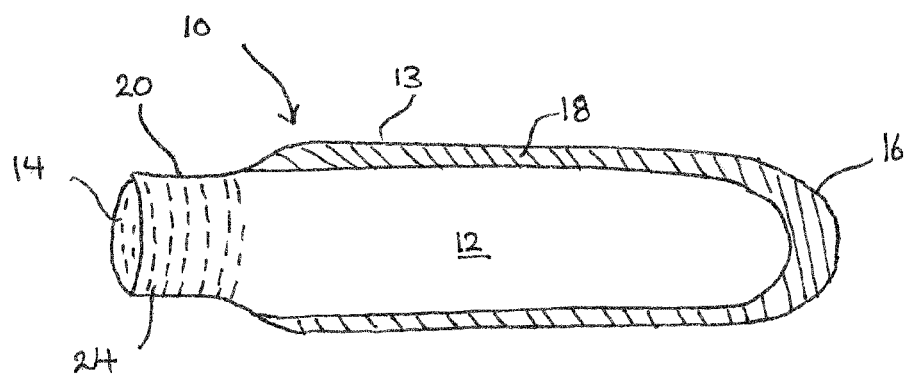
FIG. 2 is a perspective view of a second embodiment of a hygienic article for a male.

Another embodiment of a hygienic article 10 is illustrated in FIG. 2. As shown in FIG. 2, the hygienic article 10 includes a tube, such as an elasticized tube 12 with a first end 14 and a closed second end 16 opposite the first end 14. The first end 14 of the elasticized tube 12 is adapted to receive a limp penis. The elasticized tube 12 is formed of breathable material 18, and the first end 14 of the elasticized tube 12 includes a retaining portion 20 adapted to apply sufficient pressure to retain the hygienic article on the penis without substantially constricting blood flow. For example, the hygienic article 10 may be worn continuously for at least 3 hours, at least 6 hours, or at least 12 hours, or more. The absorbent material 18 which absorb fluids as discussed above, extends between adjacent the first end 14 and the closed second end 16. As shown in FIG. 2, the retaining portion 20 includes an elasticized band 24 adapted to extend around the circumference of the penis to retain the hygienic article 10 on the penis. In yet another embodiment, at least a portion of the second end 16 of the elasticized tube 12 comprises absorbent material 18 adapted to absorb fluids. For example, the absorbent material 18 may be integral with the second end 16 of the elasticized tube 12.

In another embodiment, a hygienic article 10 includes an elasticized tube 12 having a first end 14 adapted to receive a limp penis and a closed second end 16 opposite the first end 14, where the elasticized tube 12 is formed of breathable material 13. The hygienic article 10 also includes a base portion adjacent the first end of the elasticized tube 12 adapted to apply sufficient pressure to retain the hygienic article 10 on the penis without substantially constricting blood flow. The hygienic article 10 also includes a tip portion adjacent the second end 16 of the elasticized material forming an enclosed end of the hygienic article 10, where at least a portion of the tip portion comprises an absorbent material 18 adapted to absorb fluids. The base portion of the hygienic article 10 may include elasticized thread or an elasticized band as discussed above. The base portion and tip portion may be integral with the elasticized tube 12 or may be formed separately and attached to the elasticized tube during manufacturing of the hygienic article 10.

Figure 3:
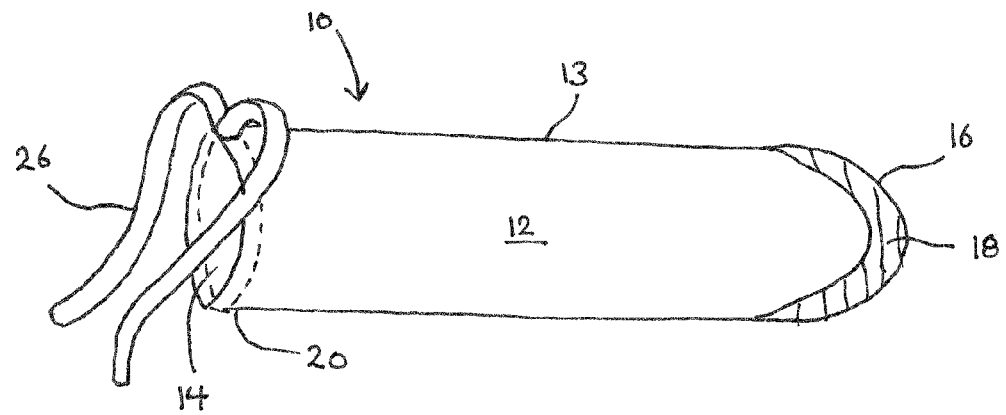
FIG. 3 is a perspective view of a third embodiment of a hygienic article for a male.

In a further embodiment, as shown in FIG. 3, a hygienic article 10 is provided that includes an elasticized tube 12 having a first end 14 adapted to receive a penis and a closed second end 16, where the elasticized tube 12 is formed of a breathable material 13. The hygienic article 10 has a retaining portion 20 adjacent the first end 14 of the elasticized tube 12 adapted to retain the hygienic article 10 on the penis without substantially constricting blood flow, and an absorbent material 18 extending at least within the second end 16 of the elasticized tube 12 adapted to absorb fluids. As shown in FIG. 3, the retaining portion 20 includes one or more ties 26 adapted to extend around the circumference of the penis to retain the hygienic article 10 on the penis. The one or more ties 26 may be elastic and may be tied into a knot, such as the bow illustrated in FIG. 3, to secure the hygienic article 10 onto the penis.

Figure 4:
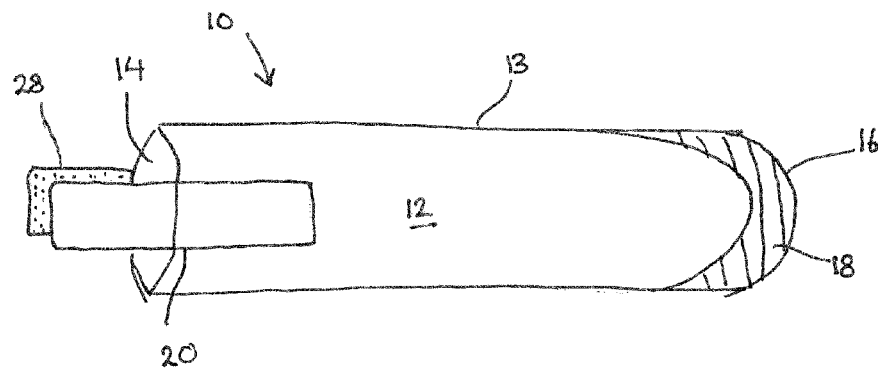
FIG. 4 is a perspective view of a fourth embodiment of a hygienic article for a male.

In yet another embodiment, the retaining portion 20 may optionally include at least one adhesive strip 28 adapted to secure the hygienic article 10 to the wearer. As illustrated in FIG. 4, the hygienic article 10 has an elasticized tube 12 with a first end 14 and a closed second end 16 opposite the first end 14. The retaining portion 20 including the at least one adhesive strip 28 is adapted to retain the hygienic article 10 on the penis without substantially constricting blood flow. The at least one adhesive strip 28 is secured to the penis or pelvic region of the wearer to retain the hygienic article 10 on the penis. Adhesive strips 28 provide for minimal compression around the base of the penis allowing the hygienic article 10 to be worn for an extended time until needing to removed or replaced.

In a further embodiment, the retaining portion 20 may include at least one strip of silicone beading adapted to retain the hygienic article 10 on the penis. Silicone beading may be applied directly to the elasticized tube 12 at the retaining portion 20, or may be attached to a further piece of elasticized fabric which may be attached to the retaining portion of the hygienic article 10. The at least one strip of silicone beading may extend around the circumference of the retaining portion or may be attached intermittently around the circumference of the retaining portion.

Figure 5:
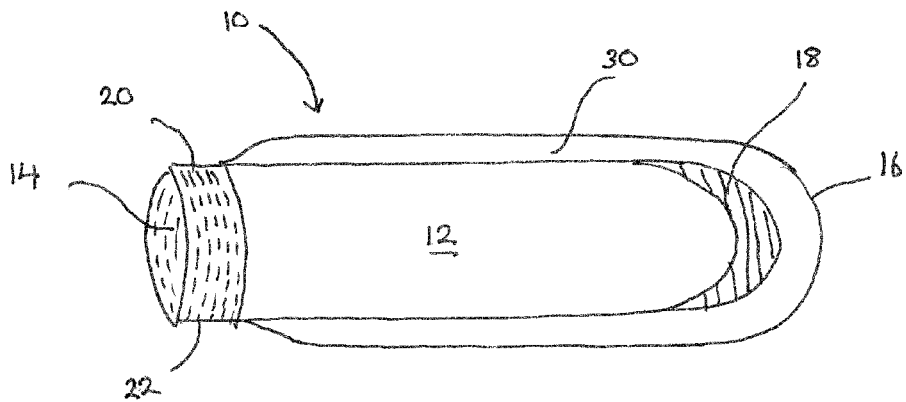
FIG. 5 is a perspective view of a fifth embodiment of a hygienic article for a male.
Figure 6:
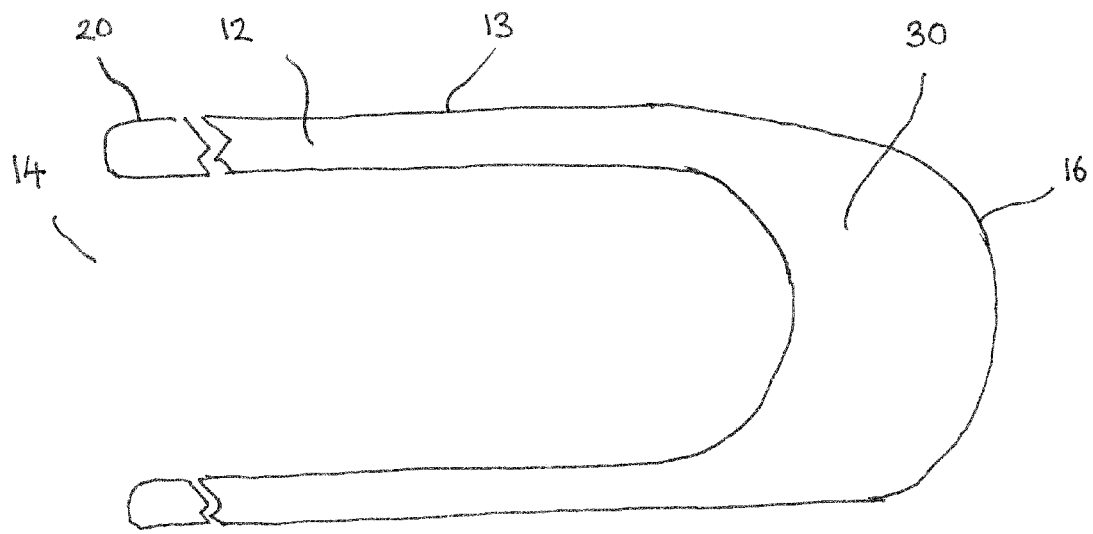
FIG. 6 is a cross-sectional view of a sixth embodiment of a hygienic article for a male.

In yet another embodiment, the hygienic article 10 further comprises padding 30 adapted to enlarge the external dimensions of the hygienic article 10. As shown in FIG. 5, padding 30 may extend substantially between the first end 14 and the second end 16 of the elasticized tube 12. Alternatively the hygienic article for a male 10 may be configured such that the padding 30 extends substantially within the second end 16, and/or on one side of the elasticized tube 12. The hygienic article 10 including padding 30 may enhance the outer aesthetic dimensions of the penis, having a similar esthetic effect as padded bras for women. Alternatively, the hygienic article 10 including padding 30 may provide additional support or protection for the penis when the hygienic article is worn in lieu of conventional underwear.

In yet another embodiment, the elasticized tube 12 of the hygienic article 10 comprises padding 30 adapted to enlarge the external dimensions of the hygienic article 30. The padding 30 may be constructed from the same material as the elasticized tube 12, such that the elasticized tube 12 is integral with the padding 30. In a further embodiment, not shown, the padding 30 and the absorbent material 18, may be constructed of the same material as the elasticized tube 12, such that the elasticized tube 12 is integral with both the absorbent material 18, and the padding 30. The padding 30 may be made from natural or synthetic materials such as cotton, wool, leather, cork, sponge, synthetic sponge, polyester or polyester mixes, plastics, neoprene, or fleece material. Constructing the various components of the hygienic article 10 of the same material may reduce manufacturing costs. Additionally, integrating the components of the hygienic article 10 may reduce the need for sewing and the number of seams, thereby reducing the possibility of leakage and improving the performance of the hygienic article 10.

Figure 7:
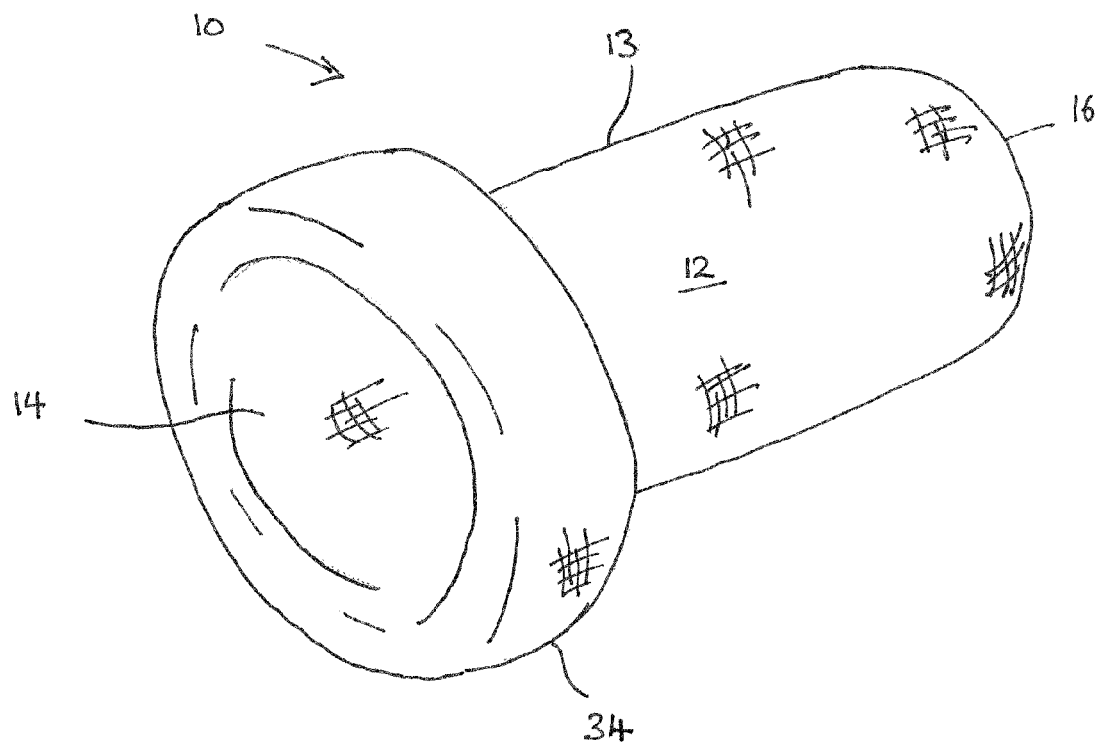
FIG. 7 is a perspective view of an embodiment of a hygienic article for a male, rolled up.

During use, the hygienic article 10 may be provided in a rolled configuration such as illustrated in FIG. 7 to assist with application of the hygienic article 10. As illustrated, the elasticized tube 12 may be rolled to form a rolled portion 34. The hygienic article 10 may then be placed on the tip of the man's penis so that the man's penis enters the hygienic article 10 through an opening 17 within the rolled portion 34 and the tip of the penis is positioned adjacent the closed second end 16. The rolled portion 34 may then be rolled down the penis so that the elasticized tube 12 substantially covers the penis with the first end 14 resting near the base of the penis. The hygienic article 10 shown in FIG. 7 provides for an easy application of the hygienic article 10 and ease of replacement when an incontinent male is in a seated or lying position, thus reducing the need to reposition the patient or resident as would be the case with traditional nappies, diapers or pads. Hygienic article 10 may be stored and packaged in the rolled configuration, as described above, such as to allow the user to open the packaging containing the hygienic article 10 and apply the hygienic article without first rolling it. Furthermore, such configuration may aid in the shipping and storage of hygienic article 10. In another embodiment, the hygienic article 10 may be adapted for repeated use. The hygienic article 10 may be washable or sanitized between uses, and the absorbent material may be replaceable.

The elasticized tube 12, of hygienic article 10, may further comprise a waterproof outer coating (not shown) adapted to prevent the movement of fluid across the waterproof outer coating, therefore preventing the ingress or egress of fluid to and from the hygienic article 10. The waterproof coating may be breathable, and may be made from plastics, cellulose-based compounds, rubber, or other waterproof materials. In an alternative embodiment, the waterproof outer coating may be integral with the elasticized tube 12.

A hygienic article for male may be configured to be particularly useful as a decorative fashion accessory or as a novelty item. The hygienic article 10 adapted for use as a fashion accessory or novelty item may comprise an elasticized tube 12 having a first end 14 adapted to receive a limp penis and a closed second end 16 opposite the first end 14, the elasticized tube 12 being formed of breathable material 13, where the first end 14 of the elasticized tube 13 comprises a retaining portion 20 adapted to apply sufficient pressure to retain the hygienic article 10 on the penis without substantially constricting blood flow, and where the elasticized tube 13 comprises padding 30 adapted to enlarge the external dimensions of the hygienic article 10, thereby increasing the apparent size of the penis. Furthermore, in circumstances where the wearer of the hygienic article 10 prefers to wear pants at a lower position, hygienic article 10, comprising padding 30, aids in supporting the pants in the desired position. The hygienic article 10 may further comprise decoration on the outer surface of the elasticized tube 12. Such decoration may comprise of a single color or a pattern to enhance the aesthetic appearance of the hygienic article 10. In another embodiment, the article 10 may be provided without padding to provide a slim protective sheathing for the penis.

Figure 8:
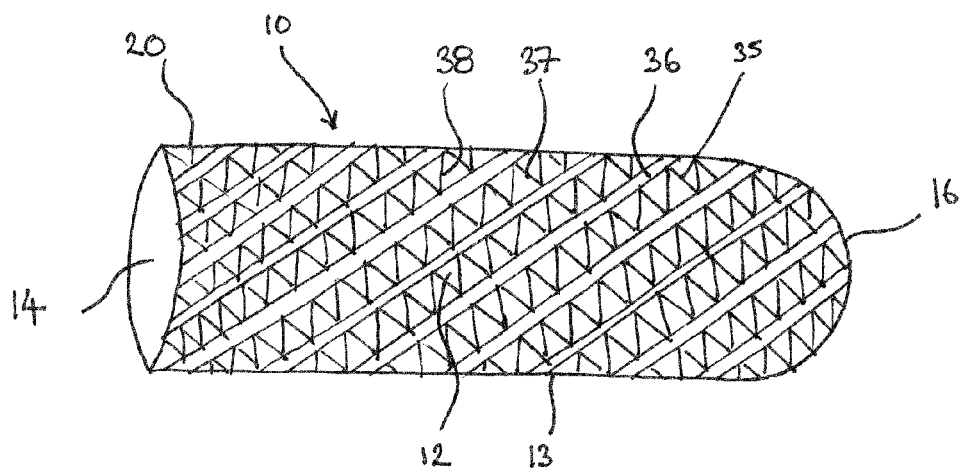
FIG. 8 is an additional embodiment of a hygienic article for a male.

FIG. 8 shows a hygienic article for a male 10 comprising an elasticized tube 12 having a first end 14 adapted to receive a limp penis and a closed second end 16, the tube 12 being formed of breathable material 13, a retaining portion 20 adjacent the first end 14 of the tube 12 adapted to retain the hygienic article 10 on the penis without substantially constricting blood flow, where the tube 12 may comprise tubular stretch net material 35. An example of tubular stretch net material is Surgilast® sold by Derma-Science, inc. FIG. 8 shows a possible configuration whereby tubular stretch net material 35 may comprise diagonal main thread 36 positioned in one direction and diagonal support thread 37 positioned in another direction, such that diagonal main thread 36 and diagonal support thread 37 form a diamond pattern. Further, tubular stretch net material may comprise of cross support thread 38 designed to increase the compressive strength of the tube 12 on the penis, without constricting blood flow. Tubular stretch net material 35 may be constructed in many different configurations and achieve the characteristics desired in the elasticized tube 12. Tubular stretch net material 35 may be made from nylon and rubber mix and may be latex-free to prevent reaction with latex-intolerant wearers of hygienic article 10.

Hygienic article 10 may be assembled such that the entire article is woven from a single material. Alternatively, if separate materials are used, or separate sections of the same material are used, the various elements may be attached using different methods. Attachment methods may include weaving, sewing, gluing, or connecting, such as with Velcro®, or any manner which may connect components together.

While certain embodiments have been described, it must be understood that various changes may be made and equivalents may be substituted without departing from the spirit or scope of the present disclosure. In addition, many modifications may be made to adapt a particular situation or material to the teachings of the disclosure without departing from its spirit or scope.

What is claimed is:

1. A hygienic article for a male comprising:
    a tube having a first end adapted to receive a limp penis within an interior of the tube, and a closed second end, the tube comprising a permeable tubular stretch net material,
    wherein the tubular stretch net material comprises a cross support thread adapted to increase a compressive strength of the tube on the penis,
    a retaining portion adjacent the first end of the tube adapted to retain the hygienic article on the penis without substantially constricting blood flow, and
    an absorbent material disposed in the interior of the tube and extending at least within the second end of the tube adapted to absorb fluids.

2. The hygienic article for a male as claimed in claim 1, where the retaining portion comprises an elasticized band adapted to extend around the penis and to retain the hygienic article on the penis.

3. The hygienic article for a male as claimed in claim 1, where the retaining portion comprises a tie adapted to extend around the circumference of the penis to retain the hygienic article on the penis.

4. The hygienic article for a male as claimed in claim 1, where the retaining portion comprises an adhesive strip adapted to be secured to the penis to retain the hygienic article on the penis.

5. The hygienic article for a male as claimed in claim 1, where the retaining portion comprises at least one strip of silicone beading adapted to non-adhesively retain the hygienic article on the penis.

6. The hygienic article for a male as claimed in claim 1, where the tube further comprises a waterproof outer coating adapted to prevent the movement of fluid across the waterproof outer coating.

7. The hygienic article for a male as claimed in claim 1, where the tubular stretch net material comprises a main thread positioned in one direction and the cross support thread positioned in another direction, such that the main thread and the cross support thread form a diamond pattern.

8. A hygienic article for a male comprising:
    a tube having a first end adapted to receive a limp penis within an interior of the tube, and a closed second end,
    a retaining portion adjacent the first end of the tube adapted to retain the hygienic article on the penis without substantially constricting blood flow,
    an absorbent material disposed in the interior of the tube and extending at least within the second end of the tube adapted to absorb fluids, and
    a padding on an exterior surface of the tube adapted to enlarge the external dimensions of the hygienic article.

9. A hygienic article for a male comprising:
    an elasticized tube having a first end adapted to receive a limp penis within an interior of the tube, and a closed second end opposite the first end, the elasticized tube comprising a permeable tubular stretch net material,
    where the permeable tubular stretch net material further comprises a main thread positioned in one direction and a cross support thread positioned in another direction, such that the main thread and the cross support thread form a diamond pattern,
    where the first end of the elasticized tube comprises a retaining portion adapted to apply sufficient pressure to retain the hygienic article on the penis without substantially constricting blood flow, and
    where at least a portion of the second end of the interior of the tube comprises an absorbent material adapted to absorb fluids.

10. The hygienic article for a male as claimed in claim 9, where the retaining portion comprises an elasticized band adapted to extend around the penis and to retain the hygienic article on the penis.

11. The hygienic article for a male as claimed in claim 9, where the retaining portion comprises a tie adapted to extend around the circumference of the penis to retain the hygienic article on the penis.

12. The hygienic article for a male as claimed in claim 9, where the retaining portion comprises an adhesive strip adapted to be secured to the penis to retain the hygienic article on the penis.

13. The hygienic article for a male as claimed in claim 9, where the retaining portion comprises at least one strip of silicone beading adapted to non-adhesively retain the hygienic article on the penis.

14. The hygienic article for a male as claimed in claim 9, where the elasticized tube further comprises a waterproof outer coating adapted to prevent the movement of fluid across the waterproof outer coating.

15. The hygienic article for a male as claimed in claim 9, where the cross support thread is adapted to increase a compressive strength of the elasticized tube on the penis.

16. A hygienic article for a male comprising:
an elasticized tube having a first end adapted to receive a limp penis within an interior of the tube, and a closed second end opposite the first end, the elasticized tube comprising a permeable tubular stretch net material,
where the first end of the elasticized tube comprises a retaining portion adapted to apply sufficient pressure to retain the hygienic article on the penis without substantially constricting blood flow, and
where at least a portion of the second end of the interior of the tube comprises an absorbent material adapted to absorb fluids, and
a padding on an exterior surface of the elasticized tube adapted to enlarge the external dimensions of the hygienic article.

17. A hygienic article for a male comprising:
an elasticized tube having a first end adapted to receive a limp penis within an interior of the tube and a second end opposite the first end, the elasticized tube comprising a breathable material, wherein the breathable material is a permeable tubular stretch net material,
where the permeable tubular stretch net material comprises a cross support thread adapted to increase a compressive strength of the tube on the penis,
a base portion adjacent the first end of the elasticized tube adapted to apply sufficient pressure to retain the hygienic article on the penis without substantially constricting blood flow, and
a tip portion adjacent the second end of the elasticized tube forming a closed end of the hygienic article, where at least a portion of the tip portion comprises an absorbent material adapted to absorb fluids.

18. The hygienic article for a male as claimed in claim 17, where the elasticized tube further comprises padding adapted to enlarge the external dimensions of the hygienic article.

19. The hygienic article for a male as claimed in claim 17, where the base portion comprises an elasticized band adapted to extend around the penis and to retain the hygienic article on the penis.

20. The hygienic article for a male as claimed in claim 17, where the base portion further comprises a tie adapted to extend around the circumference of the penis to retain the hygienic article on the penis.

21. The hygienic article for a male as claimed in claim 17, where the base portion comprises at least one strip of silicone beading adapted to non-adhesively retain the hygienic article on the penis.

22. The hygienic article for a male as claimed in claim 17, where the base portion further comprises an adhesive strip adapted to be secured to the penis to retain the hygienic article on the penis.

23. The hygienic article for a male as claimed in claim 17, where the elasticized tube further comprises a waterproof outer coating adapted to prevent the movement of fluid across the waterproof outer coating.

24. The hygienic article for a male as claimed in claim 17, where the tubular stretch net material comprises a main thread positioned in one direction and the cross support thread positioned in another direction, such that the main thread and the cross support thread form a diamond pattern.

25. The hygienic article for a male as claimed in claim 17, wherein the base portion is attached to the first end of the elasticized tube, and the tip portion is attached to the second end of the elasticized tube.

26. An article for a male comprising:
an elasticized tube having a first end adapted to receive a limp penis and a closed second end opposite the first end, the elasticized tube being formed of breathable material,
where the first end of the elasticized tube comprises a retaining portion adapted to apply sufficient pressure to retain the hygienic article on the penis without substantially constricting blood flow, and
where the elasticized tube comprises padding on an exterior surface of the elasticized tube adapted to enlarge the external dimensions of the hygienic article.

27. The hygienic article for a male as claimed in claim 26, where the breathable material comprises a cross support thread adapted to increase a compressive strength of the tube on the penis.

* * * * *